US010429300B2

United States Patent
Bosmans et al.

(10) Patent No.: US 10,429,300 B2
(45) Date of Patent: Oct. 1, 2019

(54) SURFACE PLASMON RESONANCE APPROACH TO MONITOR PROTEIN-LIGAND INTERACTIONS

(71) Applicants: The Johns Hopkins University, Baltimore, MD (US); Centre National de la Recherche Scientifique, Paris (FR); Aix-Marseilles University, Marseilles (FR)

(72) Inventors: Frank Bosmans, Annapolis, MD (US); Pierre E. Bougis, Marseilles (FR); Marie-France Eauclaire, Marseilles (FR)

(73) Assignees: The Johns Hopkins University, Baltimore, MD (US); Le Centre National de la Recherche Scientifique, Paris (FR); Aix-Marseilles University, Marseilles (FR)

( * ) Notice: Subject to any disclaimer, the term of this patent is extended or adjusted under 35 U.S.C. 154(b) by 0 days.

(21) Appl. No.: 15/545,980

(22) PCT Filed: Jan. 26, 2016

(86) PCT No.: PCT/US2016/014968
§ 371 (c)(1),
(2) Date: Jul. 24, 2017

(87) PCT Pub. No.: WO2016/123133
PCT Pub. Date: Aug. 4, 2016

(65) Prior Publication Data
US 2018/0003631 A1    Jan. 4, 2018

Related U.S. Application Data

(60) Provisional application No. 62/107,956, filed on Jan. 26, 2015.

(51) Int. Cl.
| | | |
|---|---|---|
| *G01N 21/552* | (2014.01) | |
| *G01N 33/543* | (2006.01) | |
| *G01N 33/68* | (2006.01) | |
| *C12N 9/12* | (2006.01) | |
| *C07K 14/58* | (2006.01) | |

(52) U.S. Cl.
CPC ........... *G01N 21/553* (2013.01); *C07K 14/58* (2013.01); *C12N 9/1205* (2013.01); *G01N 33/54373* (2013.01); *G01N 33/6872* (2013.01); *G01N 2500/04* (2013.01)

(58) Field of Classification Search
CPC ............. G01N 21/553; G01N 33/6872; G01N 2500/04; G01N 33/54373; C07K 14/58; C12N 9/1205; H02M 5/4505
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldberg | |
| 4,946,778 A | 8/1990 | Ladner et al. | |
| 5,206,347 A | 4/1993 | Ruoslahti et al. | |
| 5,264,563 A | 11/1993 | Huse | |
| 5,622,699 A | 4/1997 | Ruoslahti et al. | |
| 6,060,271 A * | 5/2000 | Walewski ............ | C07K 14/705 435/252.3 |
| 8,008,023 B2 | 8/2011 | Sallman et al. | |
| 8,796,003 B1 | 8/2014 | Dudek et al. | |
| 2006/0148104 A1 | 7/2006 | Marini et al. | |
| 2009/0264526 A1 | 10/2009 | Sallman et al. | |

OTHER PUBLICATIONS

Alabi, A. A. et al.: "Portability of paddle motif function and pharmacology in voltage sensors."; Nature, 2007, 450:370-375.
Bende, N. S. et al.: "A distinct sodium channel voltage-sensor locus determines insect selectivity of the spider toxin Dc1a."; Nat Commun. 2014, 5:4350.
Bezanilla, F.: "How membrane proteins sense voltage."; Nat Rev Mol Cell Biol., 2008., 9:323-332.
Bird et al.: "Single-chain antigen-binding proteins."; Science 242:423-426, 1988. (Abstract).
Blondelle et al.: "Soluble combinatorial libraries of organic, peptidomimetic and peptide diversities"; Trends Anal. Chem. 14:83 92, 1995.
Bosmans, F. et al.: "Functional properties and toxin pharmacology of a dorsal root ganglion sodium channel viewed through its voltage sensors."; J Gen Physiol., 2011, 138:59-72.
Capes, D. L. et al.: "Domain IV voltage-sensor movement is both sufficient and rate limiting for fast inactivation in sodium channels."; 'J Gen Physiol., 2013, 142:101-112.
Chioni, A.M. et al.: "A novel polyclonal antibody specific for the Na(v)1.5 voltage-gated Na(+) channel 'neonatal' splice form."; J Neurosci Methods., 2005, 147:88-98.
Crest, M. G. et al.: "Kaliotoxin, a novel peptidyl inhibitor of neuronal BK-type Ca(2+)-activated K+ channels characterized from Androctonus mauretanicus mauretanicus venom."; J Biol Chem., 1992, 267:1640-1647.
De Kruif et al.: "Biosynthetically lipid-modified human scFv fragments from phage display libraries as targeting molecules for immunoliposomes."; FEBS Lett., 399:232 236, 1996.
Ding et al.: "Synthesis and biological activity of oligosaccharide libraries."; Adv. Expt. Med. Biol., 376:261 269, 1995. (Abstract).
Ecker et al.: "Combinatorial drug discovery: Which methods will produce the greatest value?" Bio/Technology, 13:351-360, 1995.
Gilchrist, J. et al.: "Animal toxins influence voltage-gated sodium channel function."; Handb Exp Pharmacol., 2014, 221:203-229.
Gordon et al.: "Applications of Combinatorial Technologies to Drug Discovery. 2. Combinatorial Organic Synthesis, Library Screening Strategies, and Future Directions"; J. Med. Chem., 37:1385-1401, 1994.

(Continued)

Primary Examiner — Marcela M Cordero Garcia
(74) Attorney, Agent, or Firm — DLA Piper LLP (US)

(57) ABSTRACT

The present invention provides assays utilizing SPR to detect protein-ligand interactions as well as compositions utilized is such assays.

Figures 1A, 1B, 1C:
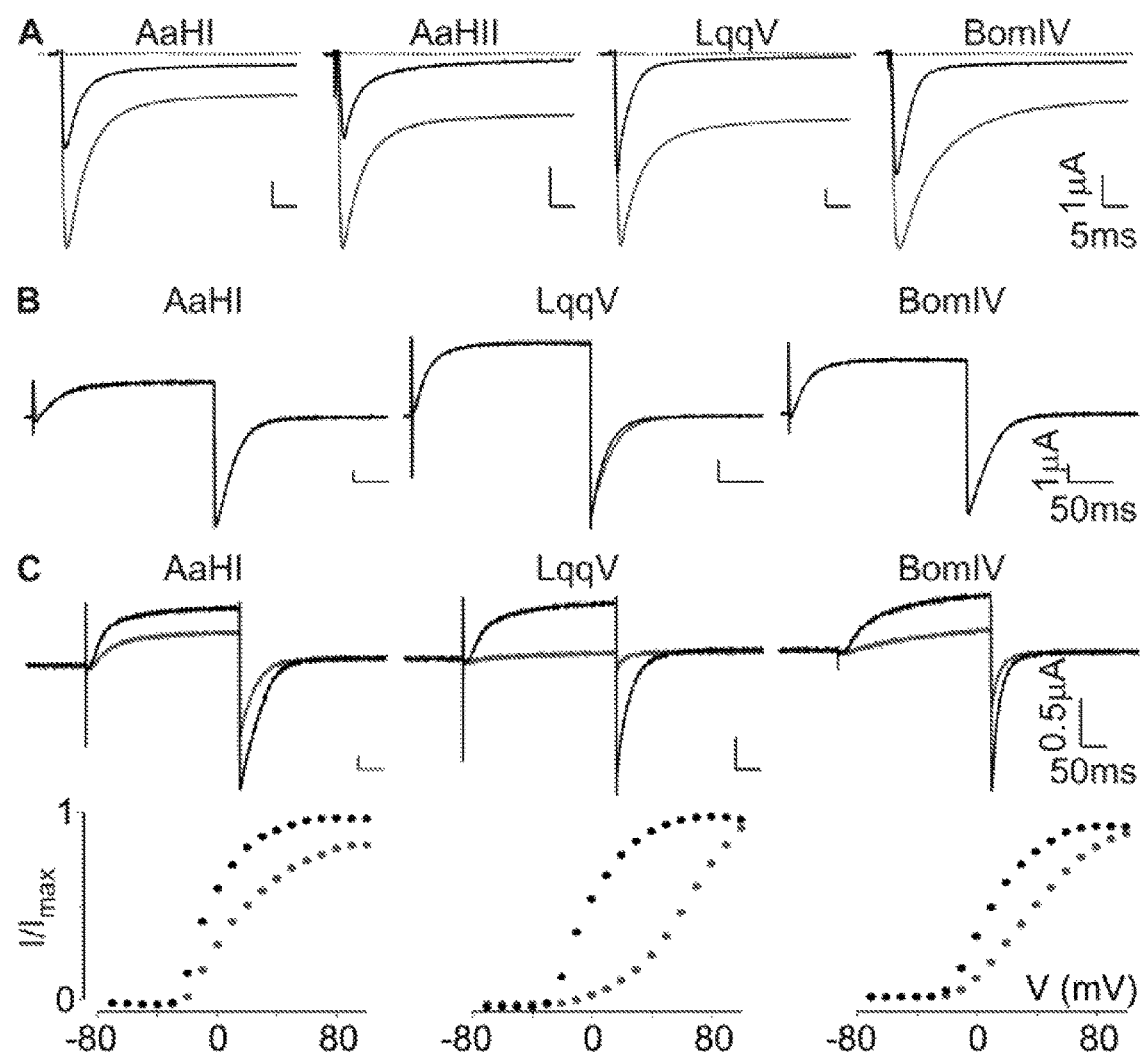

18 Claims, 4 Drawing Sheets
Specification includes a Sequence Listing.

(56) References Cited

OTHER PUBLICATIONS

Inbar et al.: "Localization of Antibody-Combining Sites within the Variable Portions of Heavy and Light Chains"; Proc. Nat'l Acad. Sci. USA 69:2659-62, 1972.

Kalia, J. et al.: "From foe to friend: Using animal toxins to investigate ion channel function."; J Mol Biol. 2014, In press.

Karaoglue et al.: "Functional Characterization of Ost3p. Loss of the 34-kD Subunit of the Saccharomyces cerevisiae Oligosaccharyltransferase Results in Biased Underglycosylation of Acceptor Substrates"; J. Cell Biol., 130:567 577, 1995.

Larrick et al.: "PCR Amplification of Antibody Genes"; Methods, 2: 106-10, 1991.

Liang et al.: "Parallel Synthesis and Screening of a Solid Phase Carbohydrate Library."; Science, 274:1520 1522, 1996. (Abstract).

Li-Smerin, Y. et al.: "Localization and molecular determinants of the Hanatoxin receptors on the voltage-sensing domains of a K(+) channel." The Journal of general physiology, 2000, 115:673-684.

Long, S. B. et al: "Atomic structure of a voltagedependent K+ channel in a lipid membrane-like environment"; Nature, 2007, 450:376-382.

Markland et al.: "Design, construction and function of a multicopy display vector using fusions to the major coat protein of bacteriophage MI3."; Gene, 109:13 19, 1991.

Murata, Y. et al.: "Phosphoinositide phosphatase activity coupled to an intrinsic voltage sensor." Nature, 2005, 435:1239-1243.

Pack et al.: "Improved bivalent miniantibodies, with identical avidity as whole antibodies, produced by high cell density fermentation of Escherichia coli.", Bio/Technology 11:1271-77, 1993.

Porter, R. R.: "The Hydrolysis of Rabbit y-Globulin and Antibodies with Crystalline F'apain"; Biochem. J., 73: 119-126, 1959.

Ramsey, I. S. et al.: "A voltage-gated protonselective channel lacking the pore domain." Nature, 2006, 440.1213-1216.

Sasaki, M. et al.: "A voltage sensor-domain protein is a voltage gated proton channel"; Science, 2006, 312:589-592.

Scott et al.: "Searching for peptide ligands with an epitope library."; Science, 249:386-390, 1990. (Abstract).

Swartz, K. J.: "Sensing voltage across lipid membranes."; Nature, 2008, 456:891-897.

Unnerstale, S. et al: "Solution structure of the HsapBK K+ channel voltage-sensor paddle sequence."; Biochemistry, 2009, 48:5813-5821.

Wang, J. V. et al.: "Mapping the receptor site for alpha-scorpion toxins on a Na+ channel voltage sensor."; Proc Natl Acad Sci U S A, 2011, 108:15426-15431.

Whitlow et al.: "Single-Chain Fv Proteins and Their Fusion Proteins"; Methods 2: 97-105, 1991.

York et al.: "The structures of arabinoxyloglucans produced by solanaceous plants."; Carb. Res., 285:99 128, 1996.

Zhang, J. Z. et al.: "Structure-function map of the receptor site for beta-scorpion toxins in domain II of voltage-gated sodium channels."; J Biol Chem., 2011, 286:33641-33651.

Bosmans et al., "Deconstructing Voltage Sensor Function and Pharmacology in Sodium Channels," Nature (2008), 456(7219):202-208.

Lee et al., "A Monoclonal Antibody that Targets a $Na_v1.7$ Channel Voltage Sensor for Pain and Itch Relief," Cell (2014), 157:1393-1404, Elsevier Inc.

Legros et al., "Engineering-Specific Pharmacological Binding Sites for Peptidyl Inhibitors of Potassium Channels into KcsA," Biochemistry (2002), 41:15369-15379, American Chemical Society.

Martin-Eauclaire et al., "A Surface Plasmon Resonance Approach to Monitor Toxin Interactions with an Isolated Voltage-Gated Sodium Channel Paddle Motif," J. Gen. Physiol. (2015), 145(2)155-162, The Rockefeller University Press.

* cited by examiner

FIG. 4

SURFACE PLASMON RESONANCE APPROACH TO MONITOR PROTEIN-LIGAND INTERACTIONS

CROSS-REFERENCE TO RELATED APPLICATIONS

This application is a 35 USC § 371 National Stage application of International Application No. PCT/US2016/014968 filed Jan. 26, 2016, now pending; which claims the benefit under 35 USC § 119(e) to U.S. Application Ser. No. 61/107,956 filed Jan 26, 2015, now expired. The disclosure of each of the prior applications is considered part of and is incorporated by reference in the disclosure of this application.

STATEMENT OF GOVERNMENT SUPPORT

This invention was made in part with government support under Grant No. R00NS073797 awarded by the National Institutes of Health. The United States government has certain rights in this invention.

INCORPORATION OF SEQUENCE LISTING

The material in the accompanying sequence listing is hereby incorporated by reference into this application. The accompanying sequence listing text file, name JHU3770_1WO_Sequence_Listing, was created on Jan. 26, 2016, and is 2 kb. The file can be assessed using Microsoft Word on a computer that uses Windows OS.

BACKGROUND OF THE INVENTION

Field of the Invention

The present invention relates generally to surface plasmon resonance (SPR), and more specifically to assays utilizing SPR to detect protein-ligand interactions as well as compositions utilized is such assays.

Background Information

Voltage-gated sodium ($Na_v$) channels constitute a welcome target for venomous animals seeking to disrupt the transmission of electrical signals to incapacitate prey or defend against predators. To this end, peptide toxins within these venoms have evolved to interact with a specific region within each of the four $Na_v$ channel voltage-sensing domains (VSDs), the S3b-S4 helix-turn-helix motif or paddle motif. The pharmacological importance of this distinct region was first recognized in voltage-gated potassium ($K_v$) channels where mutations in the S3b-S4 loop reduced channel sensitivity to hanatoxin, a founding member of the $K_v$ channel gating modifier toxin family. Later, structural information revealed that the paddle motif makes few contacts with the rest of the channel protein, which prompted experiments in which the S3b-S4 region was swapped between voltage-gated ion channels without disrupting the voltage-sensing process. The paddle motif was also identified in each of the four $Na_v$ channel voltage sensors, and transferring these regions from mammalian or insect $Na_v$ to $K_v$ channels resulted in functional $K_v$ channels that are sensitive to an array of $Na_v$ channel toxins. One recurring outcome of these studies is that $K_v$ channels containing the VSD IV paddle motif of donor $Na_v$ channels possess slower kinetics when compared with constructs containing paddle motifs from the other three VSDs. These observations fit well with the notion that VSD I-III activation in response to changes in membrane voltage is most important for channel opening, whereas VSD IV plays a distinct role in fast inactivating the channel after it has opened. As such, animal toxins that interact with the paddle motif in VSD I-III generally disrupt channel opening, whereas those that primarily target VSD IV commonly inhibit fast inactivation.

SUMMARY OF THE INVENTION

The invention is based on an approach utilizing surface plasmon resonance (SPR), an optical approach that uses polarized light to measure the refractive index near a sensor surface to which a protein of interest is attached, to analyze protein-ligand interactions.

Accordingly, in one aspect, the invention provides a method of identifying a ligand that binds to a paddle motif peptide. The method includes: a) contacting a paddle motif peptide immobilized on a sensor chip with a test molecule; and b) detecting binding of the ligand and the paddle motif peptide using surface plasmon resonance (SPR), thereby identifying the test molecule as a ligand that binds the paddle motif peptide.

In another aspect, the invention provides a sensor chip for use in a surface plasmon resonance (SPR) assay. The chip includes a paddle motif peptide immobilized thereon.

In another aspect, the invention provides a paddle motif peptide. In one embodiment the peptide includes SEQ ID NO: 2. In another embodiment, the peptide includes SEQ ID NO: 4.

In yet another aspect, the invention provides a kit including a sensor chip of the present invention as well as reagents and instructions for conducting a surface plasmon resonance (SPR) assay with the sensor chip.

BRIEF DESCRIPTION OF THE DRAWINGS

FIGS. 1A-1C are graphical representations of data illustrating that α-Scorpion toxins interact with the $rNa_v1.2a$ VSD IV paddle motif.

FIGS. 2A-2B are graphical representations of data illustrating that AaHII interacts with the $rNa_v1.2a$ VSD IV paddle motif.

FIGS. 3A-3D are graphical representations of data illustrating that α-Scorpion toxins interact with the isolated $rNa_v1.2a$ VSD IV paddle motif.

FIG. 4 is a graphical representation of data illustrating that CssIV interacts with the $rNa_v1.2a$ VSD II paddle motif.

DETAILED DESCRIPTION OF THE INVENTION

Animal toxins that inhibit voltage-gated sodium ($Na_v$) channel fast inactivation can do so through an interaction with the S3b-S4 helix-turn-helix region, or paddle motif, located in the domain IV voltage sensor. Surface plasmon resonance (SPR), an optical approach that uses polarized light to measure the refractive index near a sensor surface to which a molecule of interest is attached, was used to analyze interactions between the isolated domain IV paddle and $Na_v$ channel-selective α-scorpion toxins. The SPR analyses showed that the domain IV paddle can be removed from the $Na_v$ channel and immobilized on sensor chips, and suggest that the isolated motif remains susceptible to animal toxins that target the domain IV voltage sensor. As such, the results set forth herein uncover the inherent pharmacological sensitivities of the isolated domain IV paddle motif, which may be exploited to develop a label-free SPR approach for discovering ligands that target this region.

Before the present methods are described, it is to be understood that this invention is not limited to particular methods, and experimental conditions described, as such methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention is based on the determination that a paddle motif may remain pharmacologically functional when isolated from its channel background and immobilized on a sensor chip. This achievement provides assays geared toward discovering novel ligands having therapeutic significance that target this region. For example, recent developments with antibodies targeting $Na_v$ channel paddles suggest that they may serve as drug targets or diagnostic markers. Given its unique role in channel fast inactivation as well as its discerning sensitivity to animal toxins, the present invention focuses on the VSD IV paddle motif and provides proof-of-principle experiments for this concept by synthesizing the paddle peptide and fixing it on sensor chips to be used in surface plasmon resonance (SPR) measurements.

This label-free optical approach uses polarized light to measure the refractive index near a sensor surface to which a molecule of interest ("ligand" in SPR terminology) is attached. When a soluble particle ("analyte" in SPR terminology) binds, surface protein accumulation results in a refractive index alteration that can be measured in real time. The results are then plotted as response or resonance units (RUs) versus time in a "sensorgram." By fitting kinetics from the association and dissociation phase to a particular adsorption model, the corresponding kinetic rate constants can be calculated. Ensuing SPR experiments can determine kinetic or affinity constants between the VSD IV paddle motif and a ligand without the need for fluorescent or radioactive probe labeling.

Accordingly, in one embodiment, the invention provides a method of identifying a ligand that binds to a paddle motif peptide. The method includes: a) contacting a paddle motif peptide immobilized on a sensor chip with a test molecule; and b) detecting binding of the ligand and the paddle motif peptide using surface plasmon resonance (SPR), thereby identifying the test molecule as a ligand that binds the paddle motif peptide.

In embodiments the paddle motif peptide includes a voltage-sensing domain (VSD) of a voltage-gated channel protein which retains its biological activity when immobilized on the sensor chip.

Such voltage-gated channel protein include sodium ($Na_v$) channel proteins, potassium ($K_v$) channel proteins, and calcium ($Ca_v$) channel proteins. In the embodiment exemplified in the Examples, the voltage-gated channel protein is a sodium ($Na_v$) channel protein.

In various embodiments, the paddle motif peptide includes one or more of VSD I, VSD II, VSD III, VSD IV, or any combination thereof of a voltage-gated channel protein. In one embodiment, the paddle motif peptide includes one or more of VSD I, VSD II, VSD III, VSD IV, or any combination of a voltage-gated sodium ($Na_v$) channel protein.

A paddle motif peptide including VSD II may include SLSLMELGLANVEGLSVLRSFRLLR (SEQ ID NO: 1) or SLSLMELGLANAEGLSVLRSFRLLR (SEQ ID NO: 2).

A paddle motif peptide including VSD IV may include SIVGMFLAELIEKYFVSPTLFRVIRLARIGRI (SEQ ID NO: 3) or SIVGMFLAELIEKYFVSPTLFRVIAAARIGRI (SEQ ID NO: 4).

A test molecule or agent useful in the method of the invention can be any type of molecule. Test agents encompass numerous chemical classes, though typically they are peptides or chemical compounds, such as an organic molecule, and often are small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. If desired in a particular assay format, a candidate compound can be detectably labeled or attached to a solid support.

Methods for preparing a combinatorial library of molecules that can be tested for a desired activity are well known in the art and include, for example, methods of making a phage display library of peptides, which can be constrained peptides (see, for example, U.S. Pat. Nos. 5,622,699; 5,206,347; Scott and Smith, Science 249:386-390, 1992; Markland et al., Gene 109:13 19, 1991; each of which is incorporated herein by reference); a peptide library (U.S. Pat. No. 5,264,563, which is incorporated herein by reference); a peptidomimetic library (Blondelle et al., Trends Anal. Chem. 14:83 92, 1995; a nucleic acid library (O'Connell et al., supra, 1996; Tuerk and Gold, supra, 1990; Gold et al., supra, 1995; each of which is incorporated herein by reference); an oligosaccharide library (York et al., Carb. Res., 285:99 128, 1996; Liang et al., Science, 274:1520 1522, 1996; Ding et al., Adv. Expt. Med. Biol., 376:261 269, 1995; each of which is incorporated herein by reference); a lipoprotein library (de Kruif et al., FEBS Lett., 399:232 236, 1996, which is incorporated herein by reference); a glycoprotein or glycolipid library (Karaoglu et al., J. Cell Biol., 130:567 577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference).

The polypeptides of the present invention, such as paddle motif peptides, may be isolated and immobilized of a sensor chip. As used herein, the term "isolated" indicates that the molecule is altered by the hand of man from how it is found in its natural environment. Preferably, an "isolated" paddle motif peptide can be a "substantially purified" molecule, that is at least 60%, 70%, 80%, 90 or 95% free from cellular components with which it is naturally associated.

In embodiments, the test molecule is a protein, such as an antibody, or fragment thereof. The term "antibody" as used in this invention includes intact molecules as well as functional fragments thereof, such as Fab, F(ab')$_2$, and Fv that are capable of binding a paddle motif peptide. These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

The following example is provided to further illustrate the advantages and features of the present invention, but are not intended to limit the scope of the invention. While they are typical of those that might be used, other procedures, methodologies, or techniques known to those skilled in the art may alternatively be used.

EXAMPLE I

Surface Plasmon Resonance Approach to Monitor Toxin Interactions with an Isolated Voltage-Gated Sodium Channel Paddle Motif Surface plasmon resonance (SPR), an optical approach that uses polarized light to measure the refractive index near a sensor surface to which a molecule of interest is attached, was used to analyze interactions between the isolated domain IV paddle and $Na_v$ channel-selective α-scorpion toxins.

The following experimental materials and methods were utilized in this Example.

Two-electrode voltage-clamp recordings from *Xenopus laevis* oocytes.

The DNA sequence of rat (r)$Na_v$1.2a (provided by A. Goldin, University of California, Irvine, Irvine, Calif.), r$K_v$2.1 (provided by K. J. Swartz, National Institutes of Health), and the r$Na_v$1.2a/$K_v$2.1 VSD II or IV chimera was confirmed by automated DNA sequencing, and cRNA was synthesized using T7 polymerase (mMessage mMachine™ kit; Life Technologies) after linearizing the DNA with appropriate restriction enzymes. Channels were expressed in *Xenopus* oocytes (obtained from *Xenopus* 1) and studied after a 1-d incubation after cRNA injection (incubated at 17° C. in 96 mM NaCl, 2 mM KCl, 5 mM HEPES, 1 mM MgCl$_2$, 1.8 mM CaCl$_2$, and 50 μg/ml gentamycin, pH 7.6 with NaOH) using two-electrode voltage-clamp recording techniques (OC-725C; Warner Instruments) with a 150-μl recording chamber. Data were filtered at 4 kHz and digitized at 20 kHz using pClamp™ 10 software (Molecular Devices). Microelectrode resistances were 0.5-1.5 MΩ when filled with 3 M KCl. For K$_v$ chimera channel experiments, the external recording solution contained (mM): 50 KCl, 50 NaCl, 5 HEPES, 1 MgCl$_2$, and 0.3 CaCl$_2$, pH 7.6 with NaOH. For rNa$_v$1.2a experiments, the external recording solution contained (mM): 100 NaCl, 5 HEPES, 1 MgCl$_2$, and 1.8 CaCl$_2$, pH 7.6 with NaOH. All experiments were performed at ~22° C. Leak and background conductances, identified by blocking the channel with agitoxin-2 (provided by K. J. Swartz), have been subtracted for all of the K$_v$ channel currents shown. Tetrodotoxin (Alomone Labs) subtraction was used to isolate Na$_v$ channel currents. After the addition of the toxin to the recording chamber, the equilibration between the toxin and the channel was monitored using weak depolarizations elicited at 5- or 10-s (R1629A/L1630A mutant) intervals. Voltage-activation relationships were obtained by measuring tail currents for K$_v$ channels or steady-state currents and calculating conductance for Na$_v$ channels, and a single Boltzmann function was fitted to the data according to $I/I_{max}=[1c+cexp(-zF(Vc-cV_{1/2})/RT)]^{-1}$, where $I/I_{max}$ is the normalized tail-current amplitude, z is the equivalent charge, $V_{1/2}$ is the half-activation voltage, F is Faraday's constant, R is the gas constant, and T is temperature in kelvin. For all channels, voltage-activation relationships were recorded in the absence and presence of toxin. The ratio of currents (I/I$_0$) recorded in the presence (I) and absence (I$_0$) of toxin was calculated for voltages typically ranging from −140 to 10 cmV, depending on the construct. The value of I/I$_0$ measured in the plateau phase at voltages where toxin-bound channels do not open was taken as Fu. The apparent equilibrium dissociation constant (apparent K$_D$) for K$_v$ channels was calculated according to $K_D=((1/(1c-cFu^{1/4}))c-c1)[toxin]$, assuming four independent toxin-binding sites per channel. Results are given as mean±SEM unless noted otherwise. Offline data analysis was performed using Clampfit 10™ (Molecular Devices), Origin 8.0™ (OriginLab), and Excel™ (Microsoft). All chemicals were obtained from Sigma-Aldrich.

Peptide Synthesis.

VSD II and IV paddle peptides of rNa$_v$1.2a were produced using standard Fmoc solid-phase peptide synthesis on preloaded Fmoc-amino acid Wang resin, HPLC purified (>99.5% purity), and tested for the correct mass using mass spectrometry by ProteoGenix™. Circular dichroism (CD) measurements were performed in a standard PBS solution containing 0.1% vol/vol lauryldimethylamine N-oxide on a spectropolarimeter (J-810; JASCO).

SPR Experiments.

SPR experiments were performed at 25° C. on a Biacore™ T200 instrument (GE Healthcare) using 150 mM NaCl, 3 mM EDTA, 0.005% surfactant P20, and 10 mM HEPES-NaOH, pH 7.4, for the coupling protocol or 50 mM phosphate, pH 7.2, as running buffer. Neutravidin (Thermo Fisher Scientific) was immobilized on CM5 sensor chips (GE Healthcare) using an amine coupling chemistry. All chemicals were obtained from Sigma-Aldrich. Biotinylated paddle peptides (ligands) were injected in experimental flow cells, as well as a SNAP-25-Biotin™ peptide of comparable length (t-SNARE protein from residues 137 to 206) in control flow cells to obtain 50 or 500 fmol of immobilized peptide for kinetic or binding analysis, respectively. In all SPR experiments, nonspecific binding obtained in the control flow cell was subtracted from the signal obtained in the experimental flow cell. For qualitative binding analysis, toxins (100 nM in running buffer containing 0.1% BSA) were injected at a flow rate of 20 μl/min over 2 min. For kinetic studies, varying toxin concentrations (15-2,000 nM) were injected at a flow rate of 20 μl/min. In between injections, the surface of the sensor chip was regenerated by injecting 1 M NaCl (15 s at 30 l/min). The bulk signal caused by refractive index differences between the flow buffer and the buffer containing the analyte was systematically excluded from the data-fitting process. It is worth noting that isolating a paddle motif (ligand) can induce conformational changes that can affect toxin (analyte) efficacy. In fact, the CD spectrum in FIG. 3A suggests the presence of an unstructured VSD IV peptide region or pool (~25%), which may alter toxin susceptibility. Sensorgrams can reveal such ligand heterogeneity by displaying biphasic dissociation curves that cannot be fitted with the frequently used Langmuir model, which assumes a 1:1 stoichiometry of analyte to ligand. To account for a possible heterogeneity of surface sites, we calculated the rate constants and affinity equilibrium dissociation constants (K$_D$) for AaHII by a fit to a heterogeneous ligand model incorporated into the Biacore T200 Evaluation™ software (v1.0). This model assumes the presence of two sites on the ligand that can bind analyte and can be described by these equations in which A represents the analyte and B1/B2 represents the heterogeneous ligand:

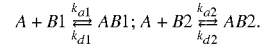

Calculating the K$_D$ values involves these components: dB1/dt=−(k$_{a1}$*A*B1−k$_{d1}$*AB1); dB2/dt=−(k$_{a2}$*A*B2−k$_{d2}$*AB2); dAB1/dt=(k$_{a1}$*A*B1−k$_{d1}$*AB1); dAB2/dt=(k$_{a2}$*A*B2−k$_{d2}$*AB2), with A=analyte concentration, B1=RU$_{max1}$ of a particular binding site, B2=RU$_{max2}$, k$_a$ and k$_d$=association and dissociation rate constant, and AB1 and AB2=0 at the start of each experiment (no complex has been formed). Note that two separate sets of k$_a$ and k$_d$ constants as well as two K$_D$ values describe each binding event.

FIGURE LEGENDS

FIGS. 1A-1C are graphical representations of data illustrating that α-Scorpion toxins interact with the rNa$_v$1.2a VSD IV paddle motif. (A) Shown is the effect of 100 nM AaHI, AaHIII, LqqV, and BomIV on rNa$_v$1.2a channel function. Representative sodium currents were elicited by a 50-ms depolarization to a suitable membrane voltage (−20 to −15 mV) before (black) and after toxin addition (green) from a holding voltage of −90 mV. Clearly, toxin application results in a large persistent current component at the end of the test pulse. Fitting the current decay with a single-exponential function before and after toxin application yields fast inactivation time constants (τ) of 3.2±0.1 and 4.7±0.1 (AaHI); 3.6±0.2 and 4.9±0.1 (AaHIII); 2.5±0.1 and 4.6±0.1 (LqqV); and 2.9±0.1 and 8.5±0.1 (BomIV), with n=3 for each value (mean±SEM). (B) Shown is the effect of 1 μM AaHI, LqqV, and BomIV on WT rK$_v$2.1. For each toxin, K$^+$ currents were elicited by a 300-ms depolarization to 0 mV from a holding voltage of −90 mV (tail voltage was −60 mV). Currents are shown before (black) and in the presence of toxin (green). (C) Effect of 100 nM AaHI, LqqV, and BomIV on the rNa$_v$1.2a/K$_v$2.1 VSD IV paddle chimera. For each toxin, K$^+$ currents (top) were elicited by a 300-ms depolarization near the foot of the voltage-activation curve (bottom) from a holding voltage of −90 mV. Currents are shown before (black) and in the presence of toxin (green). Representative normalized tail current voltage-activation relationships are shown (bottom), where tail current amplitude (I/I$_{max}$) is plotted against test voltage (V) before (black) and in the presence of toxins (green). A Boltzmann fit of the obtained data (n=3; mean±SEM) reveals a depolarizing shift in midpoint (V$_{1/2}$) of ~15 mV for AaHI, >50 mV for LqqV, and ~26 mV for BomIV. Holding voltage was −90 mV, and the tail voltage was −60 mV.

Figures 2A, 2B:
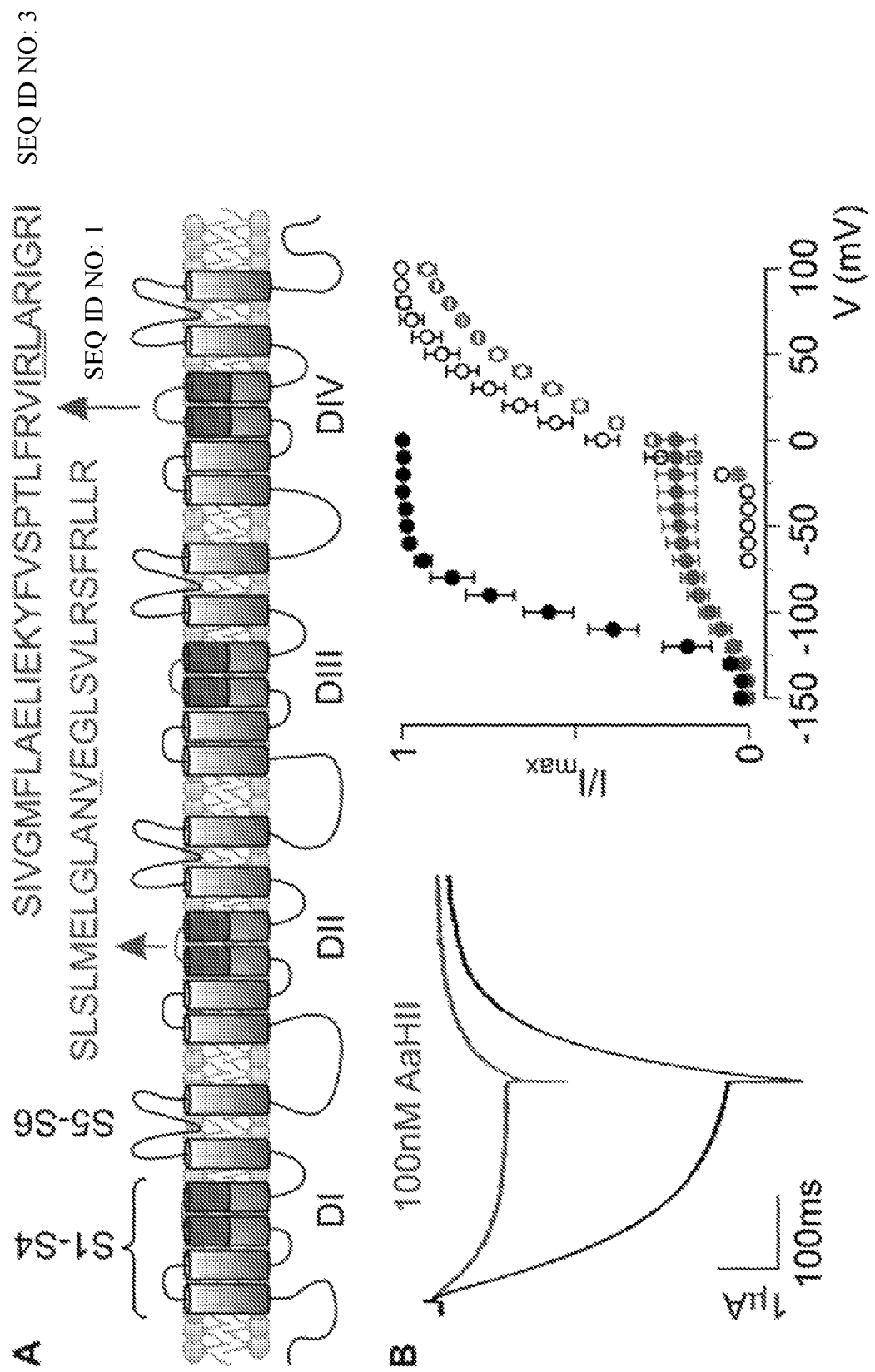

FIGS. 2A-2B are graphical representations of data illustrating that AaHII interacts with the rNa$_v$1.2a VSD IV paddle motif. (A) Na$_v$ channel cartoon embedded in a lipid membrane. Each domain (DI-IV) consists of six transmembrane segments (S1-S6) of which S1-S4 form the VSD and the S5-S6 segments of each domain form the pore. Paddle motif amino acid sequences are shown for VSD II (SEQ ID NO: 1) and IV (SEQ ID NO: 3). Underlined residues were mutated as reported in Results. (B) Effect of 100 nM AaHII on the rNa$_v$1.2a/K$_v$2.1 VSD IV chimera containing the R1629A/L1630A substitutions. K$^+$ current (left) was elicited by a 300-ms depolarization to −100 mV (tail voltage was −150 mV) after a 500-ms step to −150 mV from a holding voltage of −10 mV (near the Nernst potential for K$^+$). The data show a clear toxin-induced inhibition of the double mutant channel (black, control; green, 100 nM AaHII). Right panel displays normalized tail current voltage-activation relationships of the rNa$_v$1.2a/K$_v$2.1 VSD IV chimera without (open circles) and with the R1629A/L1630A substitutions (closed circles) where tail current amplitude (I/I$_{max}$) is plotted against test voltage before (black) and in the presence of 100 nM AaHII (green). Holding voltage for the mutant was −10 mV, followed by a 500-ms hyperpolarizing step to −150 mV to close all channels. Next, 10-mV step depolarizations of 300 ms (V) were trailed by a 300-ms tail voltage step to −150 mV (I). A Boltzmann fit of the obtained data (n=3; error bars represent mean±SEM) reveals a shift in midpoint (V$_{1/2}$) for the double mutant (−105±1 mV; slope, 17.1±1.0) compared with the rNa$_v$1.2a/K$_v$2.1 VSD IV chimera (7±2 mV; slope, 17.3±1.6). Moreover, 100 nM AaHII strongly inhibits the double mutant (apparent K$_D$=193±42 nM), whereas the rNa$_v$1.2a/K$_v$2.1 VSD IV chimera is influenced less (apparent K$_D$=1,008±92 nM), with n=3 for each value (error bars represent mean±SEM).

FIGS. 3A-3D are graphical representations of data illustrating that α-Scorpion toxins interact with the isolated rNa$_v$1.2a VSD IV paddle motif. (A) Shown are the CD spectra of the rNa$_v$1.2a VSD II and IV paddle peptides used in this paper. Analysis of both spectra revealed the presence of ~75% structured (α-helix/β-sheet) and ~25% unstructured peptide. Inset shows the crystal structure of the NavAb voltage sensor (3RVY) in which the paddle motif is indicated in green; wheat shows S1 and S2 helices, and white indicates the portion of S3 and S4 helices outside the paddle. (B) Representative association and dissociation kinetic curves obtained using SPR after the application of varying concentrations of AaHII (15-2,000 nM) over a sensor chip to which 50 fmol of the rNa$_v$1.2a VSD IV paddle peptide was linked. Toxin was applied after obtaining a steady baseline. Colored traces represent toxin binding obtained after subtraction of the signal from the control flow cell. Green dotted lines depict a fit of the data to a heterogeneous surface ligand model, a typical SPR analysis method, which yielded a high affinity K$_{D1}$ of 479±241 nM (RU$_{max1}$=135) and a lower affinity K$_{D2}$ of 747±203 nM (RU$_{max2}$=23; n=3; all results presented as mean±SD). The respective contributions of RU$_{max1}$ (~85%) and RU$_{max2}$ (~15%) to the overall RU$_{max}$ (100%) are reminiscent of the percent structured (~75%) versus unstructured (~25%) paddle peptide as observed in the CD spectrum. Toxin concentrations are indicated on the right in a shade of gray corresponding to the sensorgram. (C) Representative SPR traces after the application of 100 nM KTX, AaHI, AaHII, LqqV, BomIV, TsVII, and CssIV over a sensor chip to which the rNa$_v$1.2a VSD II (left) or IV (right) paddle peptide (500 fmol) was linked. Toxin was applied after obtaining a steady baseline. (D) Binding capacities of 100 nM α-scorpion toxins AaHI, AaHII, LqqV, the α-like scorpion toxin BomIV, and the β-scorpion toxins TsVII and CssIV to the VSD II and IV paddle motifs using SPR (error bars represent±SEM). Y-axis represents the maximum RUs obtained after toxin application. Note that 500 fmol paddle peptide was used in C and D as opposed to 50 fmol in B. As a result, RUs differ by a factor of ~10.

Figure 4:
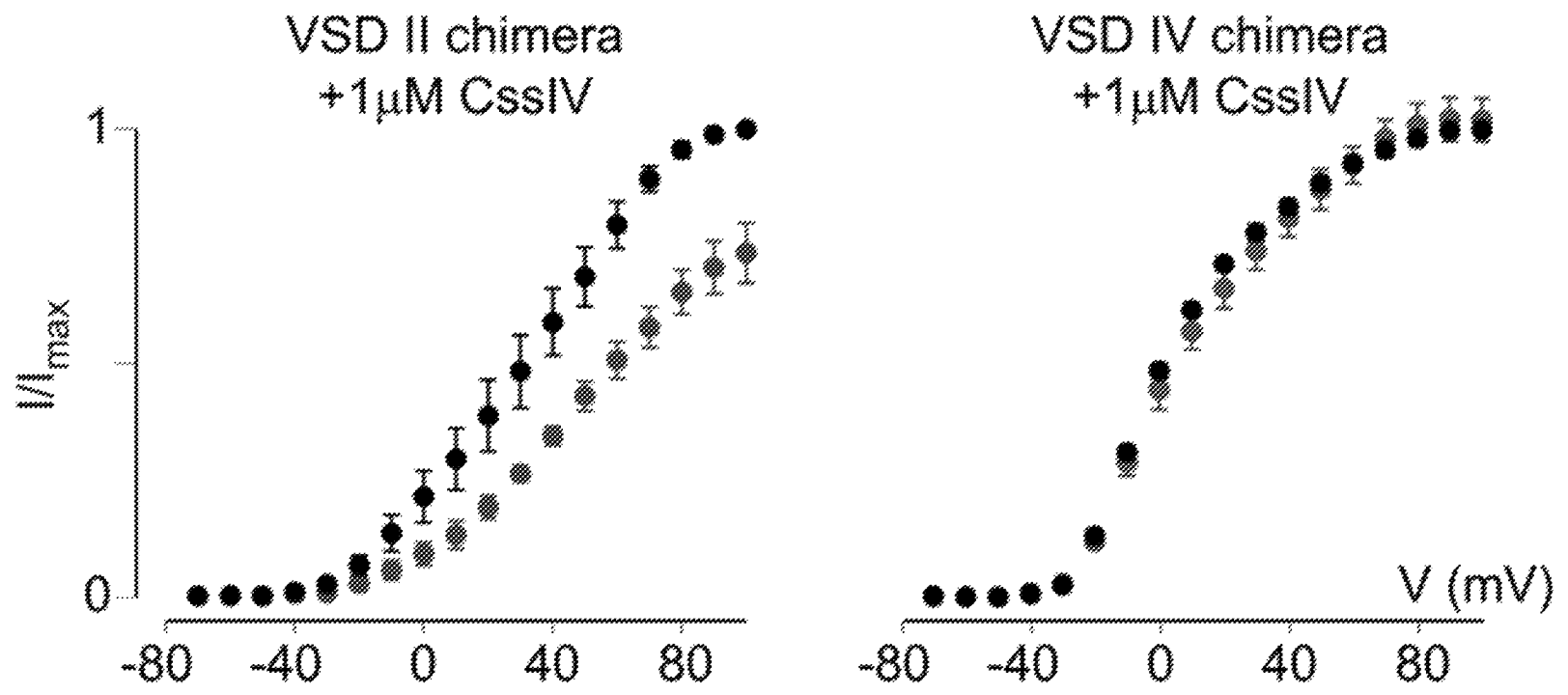

FIG. 4 is a graphical representation of data illustrating that CssIV interacts with the rNa$_v$1.2a VSD II paddle motif. Shown is the effect of 1 μM CssIV on the rNa$_v$1.2a/K$_v$2.1 VSD II and IV paddle chimera. Normalized tail current voltage-activation relationships in which the tail current amplitude (I/I$_{max}$) is plotted against test voltage (V) before (black) and in the presence of toxin (red/green) are displayed. A Boltzmann fit of the obtained data (n=3; error bars represent mean±SEM) reveals a depolarizing shift in V$_{1/2}$ of ~14 mV (from 33±2 mV to 47±1 mV) for the VSD II chimera, whereas 1 μM CssIV does not influence the VSD IV chimera. Holding voltage was −90 mV, and the tail voltage was −60 mV.

Results

The four Na$_v$ channel-selective α-scorpion toxins we selected for our experiments were AaHI and AaHII from *Androctonus australis hector*, LqqV from *Leiurus quinquestriatus hebraeus*, and BomIV from *Buthus occitanus mardochei* (Martin-Eauclaire et al. (2000) Springer, Basel: 152-168 10.1007/978-3-0348-8466-2_10; and Bende et al. (2014) Nat. Commun. 5:4350 10.1038/ncomms5350). As negative control, kaliotoxin (KTX) from *Androctonus mauretanicus* was applied, which blocks the K$_v$1.1 and K$_v$1.3 pore but does not influence Na$_v$ channel function. All toxins were purified to homogeneity as reported previously and tested for functionality on the rNa$_v$1.2a isoform expressed in *Xenopus* oocytes. In all cases, the application of 100 nM AaHI, AaHII, LqqV, or BomIV inhibits rNa$_v$1.2a fast inactivation, resulting in the appearance of a large persistent current at the end of a 50-ms test pulse (FIG. 1A). Because AaHII has already been shown to bind to the VSD IV paddle motif in rNa$_v$1.2a, it was verified if this was also the case with AaHI, LqqV, and BomIV. To this end, it was tested whether 100 nM of each toxin influenced the function of a previously constructed chimera in which the S3b-S4 region of the homotetrameric K$_v$2.1 channel was swapped for the corresponding WT region in VSD IV from rNa$_v$1.2a. As a result, a robust voltage-dependent K$^+$ current inhibition was observed, whereas WT K$_v$2.1 is insensitive, suggesting that AaHI, LqqV, and BomIV indeed interact with the transferred VSD IV paddle motif (FIGS. 1B and 1C).

To design the best possible environment for detecting toxin-paddle interactions in the SPR experiments, the isolated VSD IV paddle peptide of rNa$_v$1.2a as defined previously (Bosmans et al. (2008) Nature. 456:202-208 10.1038/nature07473) was synthesized with two amino acid substitutions (R1629A/L1630A) that each were shown to increase susceptibility to the model toxin AaHII (FIG. 2A). Specifically, the affinity of AaHII for the WT rNa$_v$1.2a/K$_v$2.1 VSD IV chimera (apparent K$_D$=1,902±102 nM) increased to 235±24 nM (R1629A) and 205±23 nM (L1630A). To verify the affinity of AaHII for the double mutant, R1629A/L1630A was introduced into the rNa$_v$1.2a/K$_v$2.1 VSD IV chimera and the construct expressed in *Xenopus* oocytes. Compared with the tail current voltage-activation relationship of the WT chimera, the R1629A/L1630A substitutions cause a striking hyperpolarizing shift in midpoint (ΔV$_{1/2}$ of approximately −112 mV; FIG. 2B). However, it is also clear that 100 nM AaHII strongly inhibits the double mutant, whereas the WT rNa$_v$1.2a/K$_v$2.1 VSD IV chimera is influenced to a much lesser extent (FIG. 2B).

Figures 3A, 3B, 3C, 3D:
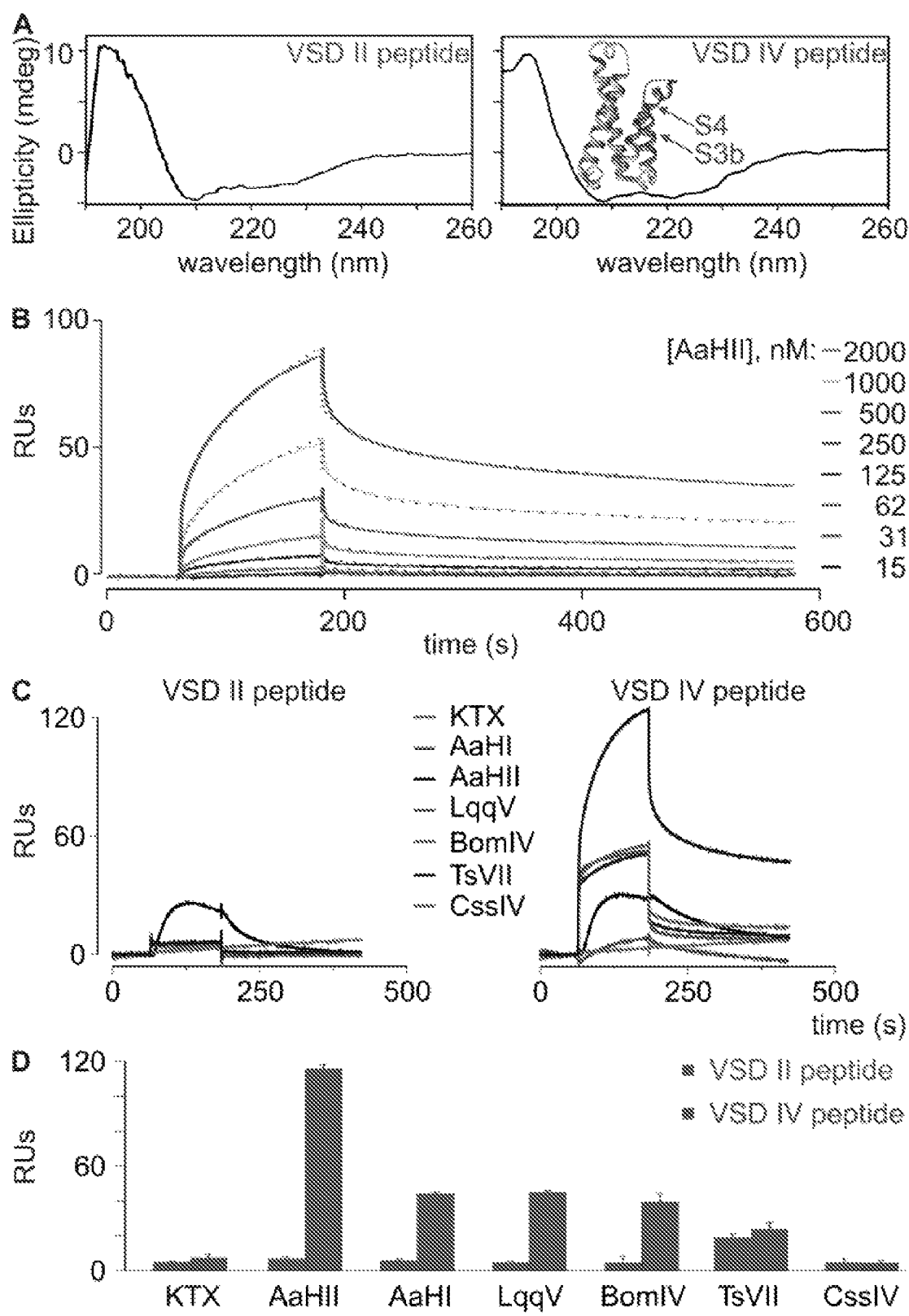

Next, the VSD IV peptide was fixed on SPR sensor chips by adding a K-linked biotin group to the C terminus, resulting in a 32-amino acid peptide altogether (SEQ ID NO: 4 which is mutated SEQ ID NO: 3 of FIG. 2A). This biotin moiety may improve toxin access to its binding site and avoid steric hindrance when the paddle peptide is linked to the sensor chips. Also, the biotin group was attached to the C terminus, as amino acids crucial for AaHII binding are mostly located at the N-terminal region of the rNa$_v$1.2a VSD IV paddle. CD measurements reveal that the peptide folds and mainly adopts an α-helical conformation (~53%; FIG. 3A), an observation that fits well with an earlier report about the NMR solution structure of an isolated paddle motif from the HsapBK K$_v$ channel. To serve as a control for toxins interacting exclusively with the VSD IV paddle motif, the previously defined VSD II paddle motif of rNa$_v$1.2a was also synthesized, including a V843A gain-of-function mutation and a C-terminal K-linked biotin group. Altogether, this peptide comprises 26 amino acids (SEQ ID NO: 2 which is mutated SEQ ID NO: 1; FIG. 2A), and similar to VSD IV, CD measurements of the VSD II paddle motif reveal a folded peptide that mainly adopts an α-helical conformation (FIG. 3A). For SPR experiments, biotinylated paddle peptides were injected in experimental flow cells to obtain ~50 or 500 fmol of immobilized peptides for kinetic or binding analysis, respectively.

The interaction of AaHII with the VSD IV paddle motif was initially examined using toxin concentrations ranging from 15 to 2,000 nM. As shown in FIG. 3B, concentration-dependent association and biphasic dissociation curves ranging from 0 to 100 RUs were obtained, thereby suggesting a possible heterogeneity of biosensor surface sites that may be related to toxin interaction with an unstructured paddle motif region (see FIG. 3A and materials and methods). Fits of these sensorgrams using a heterogeneous ligand model yielded two sets of association (k$_a$) and dissociation (k$_d$) rates, i.e., k$_{a1}$=2.33×10$^3$±0.91×10$^3$ M$^{-1}$ s$^{-1}$ and k$_{a2}$=3.82×10$^4$±0.47×10$^4$ M$^{-1}$ s$^{-1}$, and k$_{d1}$=9.79×10$^{-4}$±1.40× 10$^{-4}$ s$^{-1}$ and k$_{d2}$=2.81×10$^{-2}$±0.58×10$^{-2}$ s$^{-1}$, resulting in a high affinity K$_{D1}$ (k$_{d1}$/k$_{a1}$) of 479±241 nM (RU$_{max1}$=135) and a lower affinity K$_{D2}$ (k$_{d2}$/k$_{a2}$) of 747±203 nM (RU$_{max2}$=23), which may represent a partially active binding site (n=3; all results presented as mean±SD). Although comparing diverse affinity measurements obtained from different systems is not straightforward, K$_{D1}$ resembles that observed when determining the susceptibility of the rNa$_v$1.2a/K$_v$2.1 VSD IV R1629A/L1630A paddle chimera for AaHII (apparent K$_D$ is 193±42 nM; FIG. 2B). The affinity of the toxin for WT rNa$_v$1.2a is ~5 nM, suggesting that regions outside of the VSD IV paddle motif may enhance toxin efficacy. However, such secondary interactions seem more crucial for toxins interacting with VSD II, a notion that is explored in the next section. Overall, the biological activity of AaHII in this SPR assay suggests an intrinsic pharmacological sensitivity of the isolated rNa$_v$1.2a VSD IV paddle motif and demonstrates the effectiveness of the SPR technique in determining ligand interactions with this region. In contrast to the VSD IV peptide, an effect of AaHII was not noticed when applying up to 20 μM toxin to sensor chips coated with the VSD II paddle motif (FIGS. 3C and 3D). In concordance, no interaction was observed when assaying AaHII on the rNa$_v$1.2a/K$_v$2.1 VSD II paddle chimera. To further evaluate the robustness of the SPR approach reported here, it was examined whether the α-scorpion toxins AaHI, LqqV, and BomIV also interact with the isolated VSD IV paddle peptide at a concentration of 100 nM. It was indeed determined that all four toxins bind this motif with RUs of ~40-60, whereas a response was not obtained when testing the VSD II peptide (FIGS. 3C and 3D).

To verify the proper function of the VSD II paddle motif peptide in this SPR assay, 100 nM TsVII was first applied, a β-scorpion toxin from the Brazilian scorpion *Tityus serrulatus*, which promotes opening of rNa$_v$1.2a (apparent K$_D$ ranges from 25 to 121 nM) by primarily interacting with the paddle motif in the domain II voltage sensor with an apparent K$_D$ of 112±12 nM. However, electrophysiological data from the rNa$_v$1.2a/K$_v$2.1 chimeras revealed that TsVII can also bind to the VSD IV paddle. In concert, both paddle motifs responded to the presence of TsVII in SPR experiments (FIGS. 3C and 3D), thereby indicating that sensor chips containing the VSD II or IV paddle motifs are capable of binding appropriate ligands. Also, the K$_v$ channel toxin KTX serving as a negative control did not bind to either of the two paddle motif peptides (FIGS. 3C and 3D). In contrast to α-scorpion toxins for which an interaction with the VSD IV paddle motif seems sufficient to exert their effect, it is important to mention that residues outside of the VSD II paddle motif are required for proper binding of β-scorpion toxins such as CssIV from *Centruroides suffusus suffusus*. Because these interactions are lost when isolating the VSD II paddle motif on an SPR chip, it is reasonable to assume that the assay may not detect binding of particular β-scorpion toxins. To investigate this possibility, it was tested whether CssIV elicited an SPR response when applied to the VSD II or IV paddle motif. Indeed, no RUs could be detected upon the addition of 100 nM CssIV (FIGS. 3C and 3D), a concentration that clearly influences WT rNa$_v$1.2a gating. Correspondingly, 1 μM CssIV is required to begin inhibiting the rNa$_v$1.2a/K$_v$2.1 VSD II paddle chimera (FIG. 4), thereby supporting the notion that regions outside of the paddle motif may indeed be crucial for β-scorpion toxin binding. Subsequently, the SPR approach described here is limited to detecting ligand interactions that do not require Na$_v$ channel regions outside of the paddle region.

DISCUSSION

Collectively, these results suggest that the VSD IV paddle motif as described in this work is a self-contained unit that retains its pharmacological sensitivities toward α-scorpion toxins when isolated from the rest of the Na$_v$ channel (FIG. 3). As such, it is proposed that a label-free SPR method may be used to detect interactions between ligands and Na$_v$ channel paddle motifs without the need to express the full-length channel in a heterologous expression system. Because a full measurement cycle-including chip-regeneration steps—takes <10 min, this biosensor approach may constitute a first step toward designing a screening method to uncover interactions between pharmacological ligands and paddle-containing ion channels. One limitation that emerged from our experiments is the inability of this method to detect ligand interactions that require regions outside of the paddle region (e.g., CssIV; FIG. 3). However, in conjunction with a report showing that paddle motif-targeting antibodies may be therapeutically beneficial or could serve as diagnostic markers, the results reported here may open up a valuable pathway for discovering novel molecules that influence $Na_v$ channel function by interacting with the VSDs. Moreover, this methodology can be modified to conduct competition experiments in which the displacement of toxin bound to the VSD IV paddle motif by paddle-targeting drugs can be monitored. The identification of such compounds may be useful in reshaping $Na_v$ channel activity in disease conditions associated with an abnormal fast inactivation process. In a broader context, this SPR approach could help identify ligands for VSDs not associated with a pore region.

Although the invention has been described with reference to the examples herein, it will be understood that modifications and variations are encompassed within the spirit and scope of the invention. Accordingly, the invention is limited only by the following claims.

What is claimed is:

1. A method of identifying a ligand that binds to a paddle motif peptide, the method comprising:
   a) contacting a paddle motif peptide immobilized on a sensor chip with a test molecule, wherein the paddle motif peptide comprises SEQ ID NO: 2 or SEQ ID NO: 4;
   b) detecting binding of the ligand and the paddle motif peptide using surface plasmon resonance (SPR), thereby identifying the test molecule as a ligand that binds the paddle motif peptide.

2. The method of claim 1, wherein the sensor chip comprises multiple paddle motif peptides, each comprising a voltage-sensing domain (VSD) of a voltage-gated channel protein.

3. The method of claim 2, wherein the voltage-gated channel protein is selected from the group consisting of a sodium (Nav) channel protein, a potassium (Kv) channel protein, and a calcium (Cav) channel protein.

4. The method of claim 1, wherein the test molecule is a peptide.

5. The method of claim 4, wherein the peptide is an antibody, or fragment thereof.

6. The method of claim 1, wherein the method is a label free optical assay.

7. The method of claim 1, further comprising generating a sensorgram.

8. The method of claim 1, further comprising calculating a kinetic rate constant.

9. A sensor chip for use in a surface plasmon resonance (SPR) assay, the chip comprising a paddle motif peptide immobilized thereon, wherein the paddle motif peptide comprises SEQ ID NO: 2 or SEQ ID NO: 4.

10. The chip of claim 9, wherein the sensor chip comprises multiple paddle motif peptides, each comprising a voltage-sensing domain (VSD) of a voltage-gated channel protein.

11. The chip of claim 10, wherein the voltage-gated channel protein is selected from the group consisting of a sodium (Nav) channel protein, a potassium (Kv) channel protein, and a calcium (Cav) channel protein.

12. A paddle motif peptide comprising SEQ ID NO: 2.

13. The peptide of claim 12, wherein the peptide consists of SEQ ID NO: 2.

14. The peptide of claim 12, wherein the peptide is biotinylated.

15. A paddle motif peptide comprising SEQ ID NO: 4.

16. The peptide of claim 15, wherein the peptide consists of SEQ ID NO: 2.

17. The peptide of claim 15, wherein the peptide is biotinylated.

18. A kit comprising the sensor chip of claim 9, reagents, and instructions for conducting a surface plasmon resonance (SPR) assay with the sensor chip.

* * * * *

```
SEQUENCE LISTING

<160> NUMBER OF SEQ ID NOS: 4

<210> SEQ ID NO 1
<211> LENGTH: 25
<212> TYPE: PRT
<213> ORGANISM: Rattus norvegicus

<400> SEQUENCE: 1

Ser Leu Ser Leu Met Glu Leu Gly Leu Ala Asn Val Glu Gly Leu Ser
1               5                   10                  15

Val Leu Arg Ser Phe Arg Leu Leu Arg
            20                  25

<210> SEQ ID NO 2
<211> LENGTH: 25
<212> TYPE: PRT
<213> ORGANISM: Rattus norvegicus

<400> SEQUENCE: 2

Ser Leu Ser Leu Met Glu Leu Gly Leu Ala Asn Ala Glu Gly Leu Ser
1               5                   10                  15

Val Leu Arg Ser Phe Arg Leu Leu Arg
            20                  25

<210> SEQ ID NO 3
<211> LENGTH: 32
<212> TYPE: PRT
<213> ORGANISM: Rattus norvegicus

<400> SEQUENCE: 3

Ser Ile Val Gly Met Phe Leu Ala Glu Leu Ile Glu Lys Tyr Phe Val
1               5                   10                  15

Ser Pro Thr Leu Phe Arg Val Ile Arg Leu Ala Arg Ile Gly Arg Ile
            20                  25                  30

<210> SEQ ID NO 4
<211> LENGTH: 32
<212> TYPE: PRT
<213> ORGANISM: Rattus norvegicus

<400> SEQUENCE: 4

Ser Ile Val Gly Met Phe Leu Ala Glu Leu Ile Glu Lys Tyr Phe Val
1               5                   10                  15

Ser Pro Thr Leu Phe Arg Val Ile Ala Ala Ala Arg Ile Gly Arg Ile
            20                  25                  30
```